United States Patent [19]

Skalla

[11] Patent Number: 5,288,469
[45] Date of Patent: Feb. 22, 1994

[54] SURGERY PLUME FILTER DEVICE

[75] Inventor: Randy M. Skalla, Leesburg, Ga.

[73] Assignee: EnviroSurgical, Inc., Cincinnati, Ohio

[21] Appl. No.: 851,862

[22] Filed: Mar. 16, 1992

[51] Int. Cl.$^5$ .................. A61L 9/00; B01D 47/00; B01D 50/00; B01D 53/00
[52] U.S. Cl. .................. 422/171; 55/233; 261/DIG. 26; 422/4; 422/5; 422/122; 422/169; 96/134
[58] Field of Search .................. 422/171, 169, 4, 5, 422/122; 55/357, 316, 233; 261/DIG. 26

[56] References Cited

U.S. PATENT DOCUMENTS

| | | | |
|---|---|---|---|
| 3,963,463 | 6/1976 | Huppke | 55/233 |
| 3,969,479 | 7/1976 | Lonnes et al. | 422/4 |
| 4,125,589 | 11/1978 | Devries | 423/210 |
| 4,238,461 | 12/1980 | Devries | 423/210 |
| 4,425,143 | 1/1984 | Nishizawa et al. | 422/169 |
| 4,433,354 | 4/1984 | Eian | 55/387 |
| 4,604,110 | 8/1986 | Frazier | 422/122 |
| 4,624,791 | 11/1986 | Ferriss | 55/233 |
| 4,826,513 | 5/1989 | Stackhouse et al. | 55/387 |
| 4,963,134 | 10/1990 | Backscheider et al. | 55/279 |
| 5,030,423 | 7/1991 | Obee et al. | 422/122 |
| 5,108,621 | 4/1992 | Robins | 210/728 |

FOREIGN PATENT DOCUMENTS 1333635 10/1973 United Kingdom.

*Primary Examiner*—Robert J. Warden
*Assistant Examiner*—L. M. Crawford
*Attorney, Agent, or Firm*—Wood, Herron & Evans

[57] ABSTRACT

A filter device and method of filtering components from a surgery plume. The filter device is comprised of a plurality of elements which react with one or more components of a surgery plume, such as that generated during electrocautery or laser surgery. The filter device, particularly in conjunction with a separate particle filter, removes cyanide, formaldehyde, benzene, and particulates, as well as odor-causing species and moisture from the surgery plume.

18 Claims, 3 Drawing Sheets

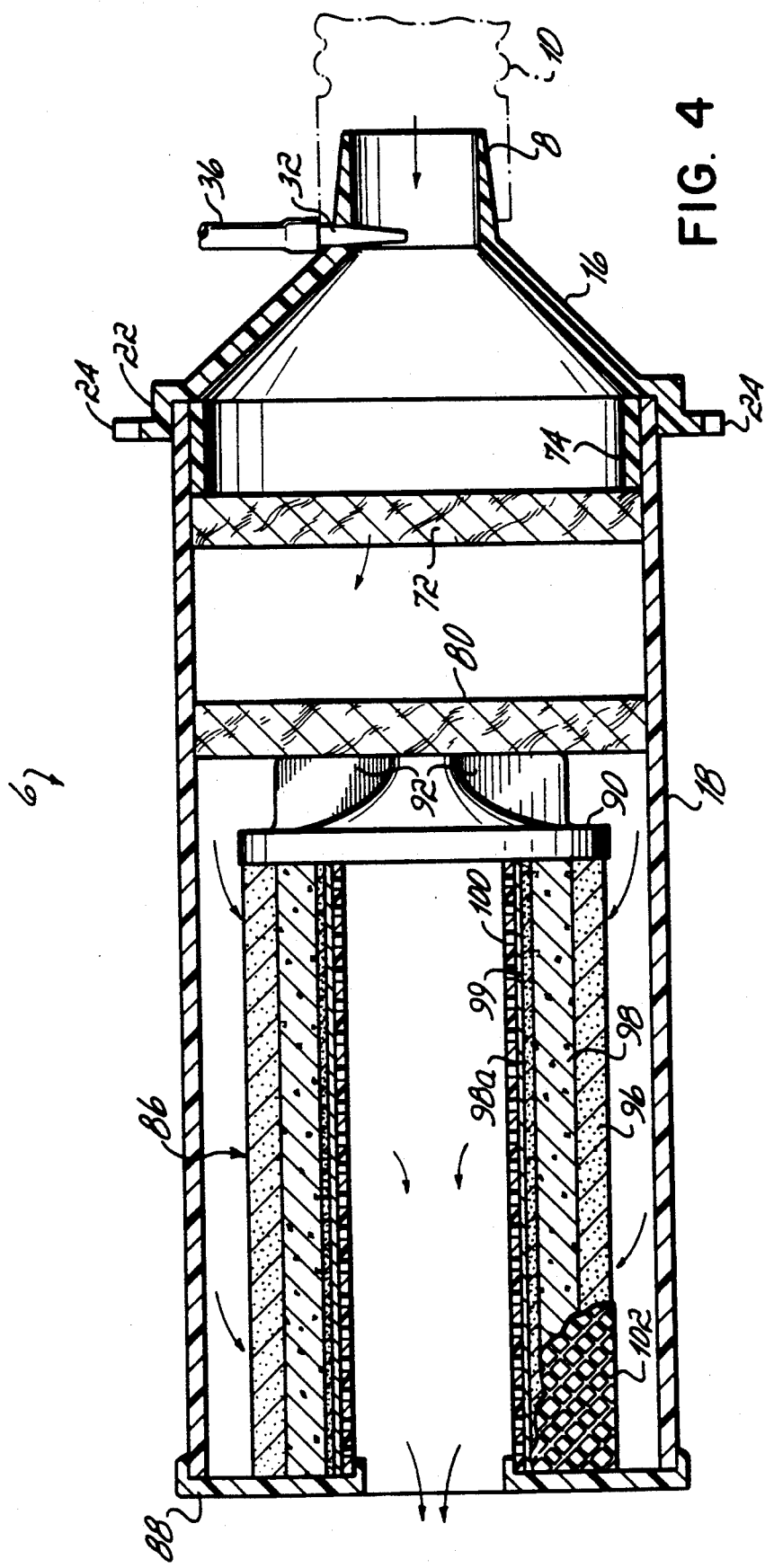

SURGERY PLUME FILTER DEVICE

FIELD OF THE INVENTION

The invention relates to a filtering device, and a method of filtering, for removing from an airstream particulates, various hazardous and odor causing chemicals. Specifically, the invention relates to a filter device for removing hazardous and odor causing species from an airstream generated in an operating room, such as by the surgical application of focused energy on tissue, as in electrocautery or laser surgery.

BACKGROUND OF THE INVENTION

It has been known for a number of years to utilize focused energy in the form of heat or electricity to burn or scar skin and underlying tissue in connection with the treatment of various ailments and disease. The practice, known as cauterization, has been particularly useful for the removal of abnormal skin growths. One drawback to the practice has been the generation of foul-smelling materials at the site resulting from the burning of the tissue. Fortunately, the volume of these materials was typically relatively low due to the type of ailments treated by the process. However, where electrocautery is used to seal blood vessels in connection with invasive surgery, the volume of materials generated is substantially increased.

Since the 1970's, lasers have been used in operating rooms to treat a wide variety of ailments. As in the traditional practice of cauterization, the laser was used to burn or sear tissue. However, because the laser was used in larger scale invasive surgery, the amount of materials generated at the site was substantially larger than that from traditional cauterization, with resulting problems related to the volume of the foul-smelling materials and the effect on operating room personnel.

The gas-generation problem has become more prevalent because in a number of surgical applications, lasers have an advantage over conventional scalpel cutting tools in that the laser is a more precise instrument, resulting in less trauma to adjacent tissue. Also, because the heat generated by the laser cauterizes the tissue as it is being cut, there is less blood loss and the healing process is speeded along.

In operation, the laser scalpel performs its cutting function by burning a narrow width of tissue. This process vaporizes moisture in the tissue and creates a smoke plume consisting primarily of water vapor, but which also includes small quantities of potentially hazardous and toxic gases, odor-causing gases, particulate matter of 1 micron or less, and bacteria and viruses.

This smoke generated by the laser scalpel, otherwise known as the laser plume, creates a variety of problems for the surgical operating team. The laser plume obscures the view of the surgeon during cutting. Further, the plume eventually deposits a coating on the mirrors used for viewing the cutting site. The operating room personnel also risk contracting infection by inhaling bacteria and virus from the tissue vaporized by the laser which are carried in the plume. The materials generated by the laser scalpel and carried in the laser plume tend to cause headaches and nausea, and more rarely nosebleeds and vomiting, which in certain instances have forced the operation to be terminated due to the sickness of the personnel. Finally, it has recently been determined that low levels of mutagenic and carcinogenic agents such as cyanide, formaldehyde and benzene are carried along in the plume.

The volume of the generated laser plume is a function of the power of the laser scalpel. As higher powered lasers are used, increasing amounts of laser plume are generated, consequently increasing the risk and discomfort to the operating team. The major lasers used in the medical and surgical fields utilize the lasing materials Neodymium-Yttrium Aluminum Garnet (Nd:YAG), Carbon Dioxide and Argon.

Early attempts to address the problem of removing the laser plume involved the use of vacuum devices fitted with an activated charcoal filter. These early devices removed the laser plume smoke from the cutting site and improved the surgeon's view of the site. However, the vacuum device could not remove all of the plume generated by high energy laser scalpels. Also, the moisture in the plume would tend to deactivate the charcoal over a period of time. Further, the charcoal filter had little or no effect on reducing the odor.

To meet the new requirements caused by the use of higher powered lasers, LASE Inc., a subsidiary of U.S. Medical Corporation, Cincinnati, Ohio, developed a smoke evacuation system incorporating an activated charcoal filter, a moisture filter before the charcoal filter to prevent deactivation of the charcoal filter, a high efficiency particle absorbing filter for capturing particles as small as 0.12 micron, a larger diameter hose to capture the increased volume of laser plume generated, and a deodorizing cartridge to mask the odor created by the plume. One type of evacuator unit used in laser surgery was the Lase System II, from U.S. Medical Corporation, and discussed in U.S. Pat. No. 4,963,134 which is incorporated herein by reference. In the middle 1980's, clinical studies were conducted which determined that amounts of mutagenic and carcinogenic agents such as cyanide, formaldehyde and benzene, and also traces of compounds such as acetone, isopropanol, cyclohexane, and toluene, are produced during the laser surgery operation. Studies also recently determined that bacteria and viruses in the tissue subjected to laser were carried in the active state in the plume. Smoke evacuation systems employing only activated carbon and a particulate filter are unable to remove the mutagenic agents, bacteria and virus species, and the odor causing species from the plume. Rather, these systems were only able to partially mask the odor causing species in the plume.

SUMMARY OF THE INVENTION

It has been an object of the invention to provide a device for filtering surgery plume such as that caused by lasers which actually removes odor from the airstream as opposed to merely masking the odor.

It has been a further object of the invention to provide a filter device which removes mutagenic and carcinogenic agents of the type detected in surgery plume.

It has been yet a further object of the invention to provide a method of removing mutagenic and carcinogenic agents and odors from surgery plume contained in an airstream.

It has been yet a further object of the invention to provide a solution for dispensing in a filter device which is particularly effective in removing mutagenic and carcinogenic agents, odors, and active bacteria and virus from an airstream incorporating a surgery plume.

It has been yet a further object of the invention to provide a filter device for removing chemical compounds and particulates from the site of the operation which would otherwise be harmful to operating room personnel.

These and other objects and advantages of the invention are obtained by a filter device for receiving an airstream having a surgery plume component such as from laser surgery which can accept the airstream at flow rates necessary for removing substantially all surgery plume from the operating area, which further can eliminate or reduce to acceptable exposure limits the known mutagenic and carcinogenic agents and odor in the surgery plume from the airstream before it exits the device. The discussion herein will use the term "surgery plume" to include not only the gaseous and particulate materials generated in electrocautery and laser surgery, but also the volatile bonding agents used in orthopedic procedures, bone tissue particles from cutting or drilling procedures, and the like.

Important to the removal of these agents from the laser plume component of the airstream is the incorporation of an oxidizing and surface active solution which is dispersed inside the device through which the surgery plume must travel. Excellent results have been obtained by dispersing the solution in the form of a foam. Foam is generated by the effect of the air entering the device and interacting with the solution. The contact time of the surgery plume with the foam containing the surface active and oxidizing component in the filter device is sufficient to break down most of the mutagenic and carcinogenic agents and odor causing species, and to kill the bacteria and virus in the surgery plume. Downstream of the foam are separate layers of a drying agent and an activated carbon filter which collect moisture and trap residual particulate species and stable but hazardous organic compounds such as benzene in the airstream. The drying agent, or desiccant, minimizes the quantity of moisture seen by the activated carbon which would otherwise coat and render inactive the absorbing surface of the carbon. An ultra low particle size absorbing filter is preferably placed in-line and downstream from the device to capture particulate matter down to 0.01 microns which would otherwise pass through the device and be exhausted to the environment.

These and other objectives and advantages of the invention are described in greater detail below, and are shown in the drawings in which:

BRIEF DESCRIPTION OF THE DRAWINGS

FIG. 4 is a cross-sectional view of the filter device with solution introduction port.

DETAILED DESCRIPTION OF THE INVENTION

Figure 1:
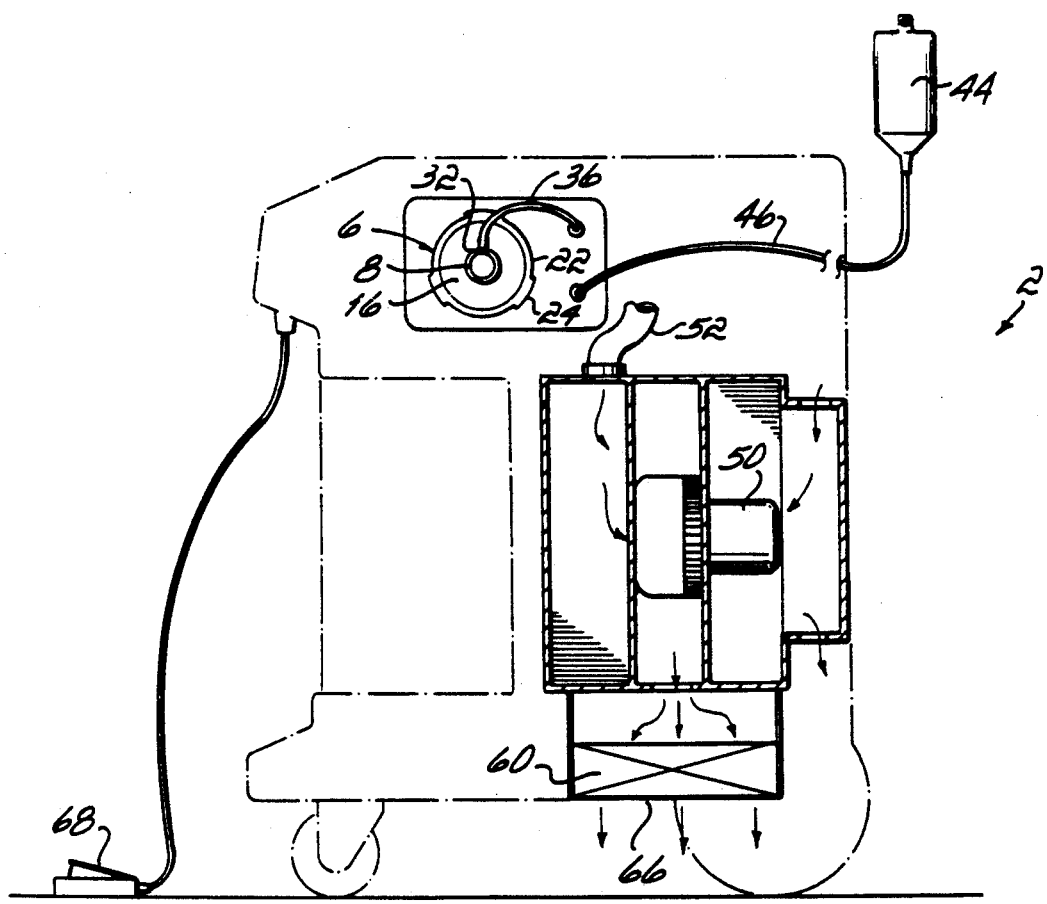
FIG. 1 is a diagrammatic view of the filter cart unit shown in phantom, which houses the filter device and interfacing equipment.

The invention in its broad aspects is adapted to accept an airstream containing gaseous and particulate materials comprising cyanide, formaldehyde, organic compounds, odor-causing species and moisture generated during cauterization or other treatment of animal tissue whereby the apparatus removes the cyanide, formaldehyde, organic compounds, odor-causing species and moisture from the airstream. The apparatus also inactivates bacteria and virus carried along in the airstream. One such apparatus is a filter assembly for receiving and treating an airstream containing gaseous and particulate materials from a surgery plume comprising a canister for retaining a plurality of filter components and having an inlet and an outlet, the inlet for receiving the airstream which contains the gaseous and particulate materials at a rate of flow; introducing means for introducing an aqueous solution comprised of oxidizing and surface active components downstream of the canister inlet; a first porous member downstream of the introducing means for receiving the aqueous solution and the gaseous and particulate materials, adapted to generate a dispersion of the aqueous solution by the interaction of the aqueous solution with the airstream through the porous member; and activated carbon in the canister through which the airstream flows. Good results have been obtained by placing in the canister downstream of the first porous member a second porous member spaced from the first to create a chamber which receives the foam.

As noted above, the surgery plume has been found to contain not only water vapor, hydrogen cyanide, formaldehyde, benzene, odor causing species which typically include additional aldehydes, and particulate matter formed during the burning process, but also bacteria and viruses. Studies have indicated that the HIV virus, among others, has been detected in the surgery plume. It is also believed that human papilloma virus (HPV) may also be transmitted in the surgery plume. Thus, it is important not only that the virus component be evacuated from the surgery site, but that it be killed before the evacuated airstream is reintroduced to the environment. In comparing the approximate particle sizes of surgery plume components, bacteria has particle diameters in the range of about 0.2 to about 25 microns ($10^{-6}$ meter), and the smoke components of the surgery plume from the laser operation have particles with diameters ranging from about 0.15 to about 8 microns, while the particle diameters of viruses reach a minimum of about 0.05 micron. A container of oxidizing solution through which an airstream is bubbled to remove virus components forms bubbles which are too large in diameter to permit adequate contact of the virus species with the oxidizing solution. It has been found that use of a foam, which is continually being broken down and reformed by the interaction of the airstream with an oxidizing solution containing a surface active component in a defined space, results in sufficient contact time with the bacteria and virus components to kill these species. Alternatively, dispersion in the form of sprays or mists may be employed, but the surface area of the oxidizing solution exposed to the airstream is not as great as the foam in a canister of equal size.

The hydrogen cyanide component of the surgery plume is oxidized by contact with the solution to form cyanate. The formaldehyde as well as any other aldehydes present in the odor causing species become oxidized or polymerized in the presence of the oxidizing solution as the airstream passes through the foam layer.

The benzene component of the surgery plume is resistant to oxidation because of its chemical stability. Nonetheless, it is removed from an airstream by passing that airstream through a layer of activated carbon which absorbs the benzene and other organic compounds. One drawback to the use of activated carbon in the same system with an aqueous solution or a moisture-laden airstream is that the moisture as it passes through the activated carbon tends to deactivate the material and render it unable to remove organic species such as benzene. Thus, it is necessary that a desiccant layer be interposed between the moisture source and the activated carbon layer to optimize the absorption ability of the carbon. So long as the airstream passing through the activated carbon layer is of approximately the same humidity as that of the surgery room, typically in the range of about sixty percent to about eighty percent relative humidity, the level of moisture is sufficiently low to maintain absorption sites on the activated carbon layer to remove the benzene and other organic components.

To provide further assurance that the formaldehyde and other aldehyde components in the surgery plume are removed by the filter device, an optional discrete porous member coated or impregnated with an aldehyde polymerizing agent may be positioned in the filter device.

The odor causing species are removed from the airstream by contact with the oxidizing component in the foam, and are further susceptible to removal as the airstream passes over the desiccant and activated carbon layers, removal being by absorption onto the surface of these layers. The oxidizing component can be one or a mixture of a number of compounds. Representative materials include but are not limited to sodium hypochlorite, sodium perborate, sodium permanganate, and sodium thiosulfate. The oxidizing agent concentration in the solution is typically in the range of about 0.5 to about 25%, by weight.

The surface active component also can be one or a mixture of a number of compounds. Representative materials include but are not limited to sodium alpha olefin sulfonate, sodium lauryl dimethylamine oxide, nonylphenol polyethylene lycol ether such as TERGITOL NP-10, and disodium oxy-bis dodecyl benzene sulfonate. The surface active component must be essentially inert to the oxidizing agent, yet be capable of contributing to the foam formation of the aqueous solution containing oxidizing agent. The surfactant concentration in the solution is typically in the range of about 1 to about 5%, by weight.

The oxidizing solution is formed by adding the surfactant component to cold water, then adding the oxidizing agent. The solution maintains optimum long-term stability if the pH is at least about 10.5, typically in the range of about 11.5 to about 12. Where the pH is very alkaline due to the addition of the surfactant, in the range of 13 to about 14, the pH can be lowered by the measured addition of sodium bicarbonate.

Representative desiccant materials are anhydrous calcium sulfate (4 mesh), amorphous silica and naturally-derived zeolites based on calcium aluminate. Activated carbon is available from Calgon, Inc., Pittsburgh, Pa., in six mesh particle size.

As an alternative to the removal of surgery plume components in a filter device utilizing in part an aqueous oxidizing solution, removal of the cyanide, formaldehyde and benzene components from an airstream has also been effected using a filter assembly without adding oxidizing solution. This assembly comprises a canister for retaining a plurality of filter components and having an inlet and an outlet, the inlet for receiving the airstream containing the gaseous and particulate materials including cyanide, formaldehyde and benzene from the surgery plume at a rate of flow, a filter member inside the canister incorporating a component which is reactive to at least the cyanide component, a discrete desiccant layer inside the canister, a filter member inside the canister incorporating a component reactive to at least the aldehyde component, and a discrete layer of activated carbon for removal of benzene and other organic compounds which is downstream of the desiccant Instead of a foam solution containing oxidizing and surface active components, the dry filter assembly utilizes discrete porous members, such as pads or sponges, coated or impregnated with oxidizing or neutralizing solutions in combination with an aldehyde polymerizing agent incorporated onto a discrete pad, and further retaining the discrete desiccant and activated carbon layers for removal of cyanide, aldehydes, and benzene and other organic compounds. The relative positions of the separate layers is not believed to affect removal capability, except that the carbon layer retains its activity longer if it is downstream of the desiccant layer.

The porous members in the dry filter assembly will include individual members coated or impregnated with compounds which are reactive to components of the surgery plume. These compounds are applied to individual porous members by dipping the members into, or spraying the member with, a solution of the agent, followed by drying. Alternatively, a dry powder containing the agent can be directly applied to the pad.

The amount of compound deposited onto the porous member is a function of the porosity and size of the member, and the concentration of the solution. Aqueous solutions which are reactive to hydrogen cyanide which were used to coat porous members include the following: 20% potassium permanganate; 50% sodium hydroxide; 20% sodium dichloro-s-triazinetrione dihydrate; 45% potassium hydroxide; 10% sodium perborate; and 20% sodium thiosulfate. The alkaline materials listed above coated onto a porous member retained cyanide, but did not convert the cyanide to any extent to a less toxic material. The above percentages are to be considered as representative only. It can be appreciated that other concentration solutions can be used for dippinq and spraying. In practice, an amount of agent must be applied which is effective to react with the airstream components over the period of time that the filter assembly is in operation.

Because live bacteria and virus are carried into the filter assembly, both with the dry filter assembly and the filter assembly utilizing the oxidizing solution, it is safer practice to dispose of the filter assembly after each use. It has been estimated that presently the maximum amount of time that a laser scalpel is used in a single operation is approximately fifteen minutes. An additional safety factor of about fifteen minutes operating time is built in, resulting in a disposable filter assembly which would be effective in removing the gaseous and particulate materials generated by current laser scalpels for a period of about thirty minutes. As surgical techniques and power levels on lasers and electrocautery knives change, the working lifetime of the disposable filter assembly will need to also be adjusted.

A material reactive to formaldehyde and other aldehydes is available commercially as Formalex ™, S & S Company of Georgia, Inc., Albany, Ga. This proprietary material removes the aldehyde component from the airstream by polymerizing the aldehyde. This material applied to a porous member at full strength and then dried was effective in removing formaldehyde from the surgery plume.

In both the wet and dry filter assemblies, minimal head pressure drop is desirable, to permit relatively high airstream flow rates with smaller vacuum units which operate relatively quietly in the operating room environment. The particulate matter in the surgery plume is partially removed as the airstream flows through the multiple porous pads, desiccant and activated carbon layers. However, remaining particulate matter down to a particle size of 0.01 micron is removed by a separate ULPA (ultra low particle absorbing) filter downstream of the filter assembly, prior to exhausting of the airstream back into the operating room environment. One such ULPA filter is manufactured by Flanders Filters.

Figure 2:
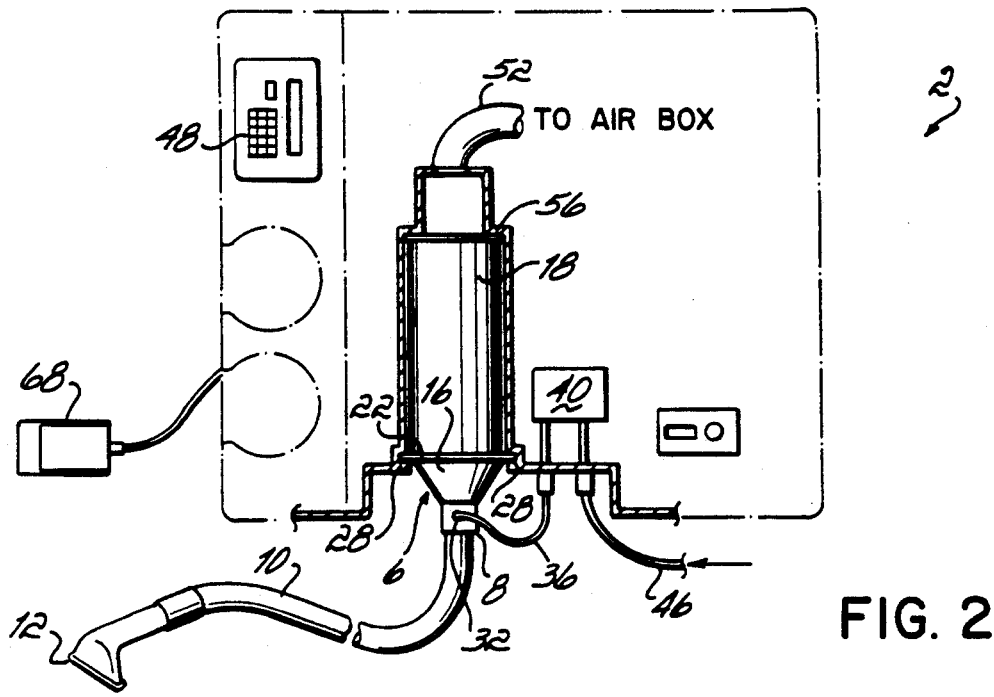
FIG. 2 is a diagrammatic top view of the filter cart unit shown in phantom, housing the filter device.

Referring to the drawings, FIGS. 1 and 2 are schematic views of the filter cart unit 2 which houses the filter assembly 6 and its complementary components. Attached to the inlet port 8 of filter assembly 6 is a flexible hose 10 with a suction tip 12 which is placed near the tissue site where the laser surgery, electrocautery, or other gaseous or particulate generating operation is taking place.

The filter assembly 6 is comprised of a cone portion 16 and a cylindrical portion 18. The cone portion 16 has an inlet port 8 at one end and is permanently attached to the cylindrical portion 18 by adhesive or heat bond, or the like, at the other end. The cone portion 16 has a raised lip 22 with tabs 24 along a portion of the raised lip 22 which fit into and lock with corresponding slots 28 in the filter cart unit 2 to retain the filter assembly 6 in position.

A feed port 32 is located on cone portion 16 at the inlet port 8 to permit introduction of an aqueous solution inside the filter assembly 6. Feed line 36 is attached to feed port 32 and connects with pump unit 40 for supplying a measured portion of oxidizing solution when the wet filter assembly is being used. Pump unit 40 in turn is connected to solution reservoir 44 outside the filter cart unit 2 via supply line 46 for supplying the needed oxidizing solution. Alternatively, the reservoir may be located inside the filter cart unit 2. Acceptable results have been obtained by suspending the solution reservoir 44 above the filter cart unit as in a plastic bag on a support such as an I.V. pole to facilitate proper flow to the pump unit 40 and thereby into the filter assembly 6. The pump unit 40 facilitates uniform, measured introduction of the oxidizing solution into the filter assembly 6, and the solution flow rate is controlled at keypad 48. However, it can be appreciated that other types of methods of fluid introduction can be utilized, even including direct gravity feed from an I.V. bag into the filter assembly 6 via the feed port 32.

Flow rates of oxidizing solution are in the range of about 2.9 to about 7.3 ml/min over the course of the run, and preferably between about 3 and 5 ml/min. As noted, a peristaltic pump such as the Model 54856-070 from VWR Scientific, Philadelphia, Pa., is useful in this application, which can provide the desired solution flow rate by varying the tubing diameter, the cycling time of the pump, or both. For the typical use period of about fifteen minutes, this flow rate provides excellent foam generation without overloading the filter assembly, as evidenced by foam appearing at the filter assembly exhaust.

The suction applied at the surgery site through suction tip 12 is created in a vacuum unit 50 which is connected to the exhaust side of filter assembly 6 through connecting line 52 and gasketed fitting 56. The vacuum unit 50 preferably generates flow rates in the range of about 35 to about 85 standard cubic feet per minute (SCFM), and more preferably between about 55 and about 70 SCFM. A representative vacuum unit is manufactured by Ametek, such as Model No. 116763-13. To minimize back flow from the vacuum unit 50 particularly after the filter assembly 6 has been removed from the cart 2 for disposal, the connecting line 52 is fitted with a flip-up shutter door (not shown) which isolates the air system.

Residual particulates in the airstream from the surgery plume which flow through the components of the filter assembly 6 down to 0.01 micron in size are trapped in the particle filter 60 directly connected to the downstream end of vacuum unit 50. After passage through particle filter 60, the airstream is exhausted to the operating room environment through cart exhaust port 66. Power to the vacuum unit 50 and pump 40 is directly controlled by foot switch 68 or by keypad 48.

As shown in FIG. 4, the filter assembly 6 receives solution through feed line 36 and feed port 32 which is blown into first dispersal pad 72 by the action of the incoming airstream as indicated by the arrow at inlet port 8. The placement of the tip of feed port 32 should be such as to obtain good dispersion of the solution droplets. The first dispersal pad 72 is porous and is constructed of material inert to the components of the surgery plume and the oxidizing solution. One type of pad is manufactured from a 60:40 blend of nylon and polyester fibers bonded with thermoplastic resin, by Americo, Inc., Atworth, Ga., discussed in more detail below. This pad spans the entire inside diameter of the cylindrical portion 18 of assembly filter 6 to prevent the airstream from bypassing the pad along the inside wall of cylindrical portion 18 and is retained in position by tube spacers 74 on the upstream side and a bead of hot melt adhesive on the upstream side of the pad which contacts both the pad and the inside circumference of the cylindrical portion 18.

Downstream of the first dispersal pad 72 is a second dispersal pad 80. This pad, like first dispersal pad 72, is secured by a bead of hot melt adhesive on the upstream side of the pad. The pad is also manufactured by Americo, Inc. and is discussed in more detail below. This second dispersal pad 80 is coated or impregnated with a formaldehyde reactive component which aids in the formaldehyde removal. An example of such a reactive component is a material sold under the name Formalex ™, available from S & S company of Georgia, Inc., Albany, Ga. Formalex ™ is a proprietary compound which serves to polymerize aldehydes, particularly formaldehyde. Alternatively, the second dispersal pad 80 can be uncoated.

Downstream of the second dispersal pad 80 is a filter cartridge 86 which is secured into the cylindrical portion 18 by a flexible plastisol end cap 88. The filter cartridge 86 has a nose section 90 with a plurality of spacer ribs 92 to deflect air along the side of the filter cartridge 86. The filter cartridge 86 has a tubular construction with an outer layer 96 comprised of a non-woven polyester substrate media impregnated with amorphous silica and serving as a desiccant, such as Lewcott Grade SG-NWPE-4.0-150. The silica is mixed with a polyvinyl acetate adhesive which is then applied to the polyester media. Inside the outer layer 96 is a first carbon tube 98, which is comprised of two wraps of a non-woven polyester substrate media impregnated with activated carbon ground and mixed with a polyvinyl acetate adhesive, such as Lewcott Grade ACF-NWPE-4.0-150. Under the first carbon layer 98 is a second carbon layer 98a, which is comprised of coal based powdered activated carbon, regenerated cellulose, cellulosic fiber and latex binder, such as Lydall Grade 703 carbon filter media. Under this layer is a cellulose layer 99, comprised of cellulose media with a trace of polyamide wet strength resin, such as Ahlstrom Grade 1278. The innermost tube in the filter cartridge 86 is a perforated tube 100 which is injection molded and made from polypropylene, available from Crellin, Inc. As shown in FIG. 4, the entire center length of the filter cartridge 86 is open, which serves as an exhaust conduit for passing the airstream out of the filter assembly 6. Structural support along the outside of the filter cartridge 86 is provided by an outer layer of low density polyethylene extruded netting 102, such as Naltex Grade 407.

Figure 3:
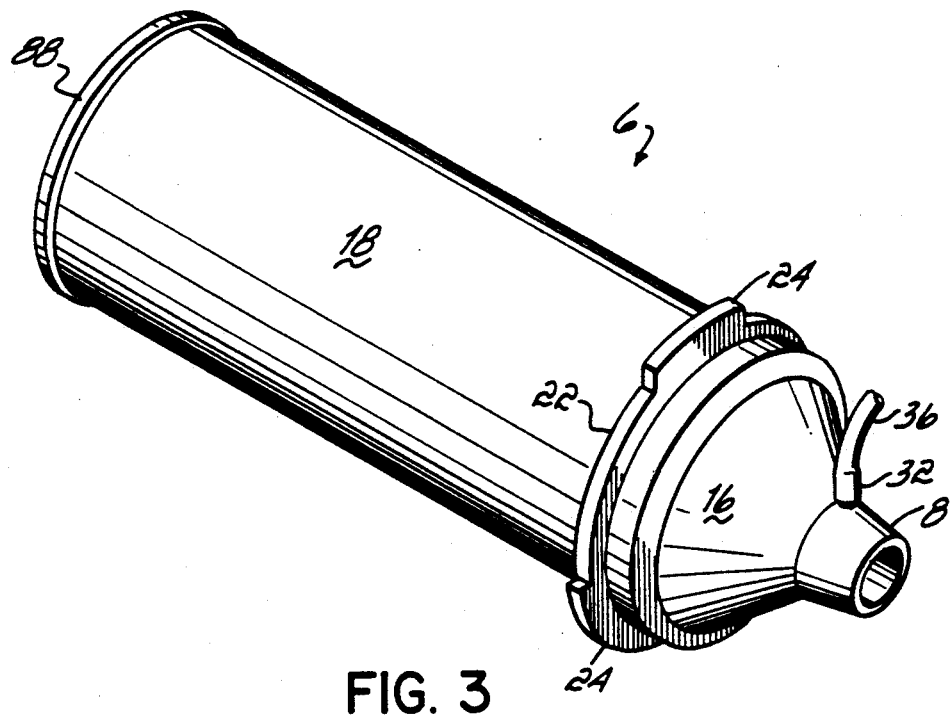
FIG. 3 is a perspective view of the filter device with attached solution inlet line.

The plastisol end cap 88 which retains the filter cartridge 86 inside cylindrical portion 18 of filter assembly 6 is ring-shaped and secures to the polypropylene perforated tube of the filter cartridge 86 and the outside surface of the cylindrical portion 18 by a bead of adhesive around the entire circumference of cylindrical portion 18. The plastisol material is a colloidal dispersal of a vinylchloride resin and a plasticizer which is FDA approved for use in potable water applications, such as Dennis Chemical Grade 9233-40. This plastisol end cap 86 is sealingly connected to the vacuum unit 50 from which the suction creating the airstream flow through filter assembly 6 is generated. The filter assembly 6 is shown as a discrete unit in FIG. 3.

Figure 5:
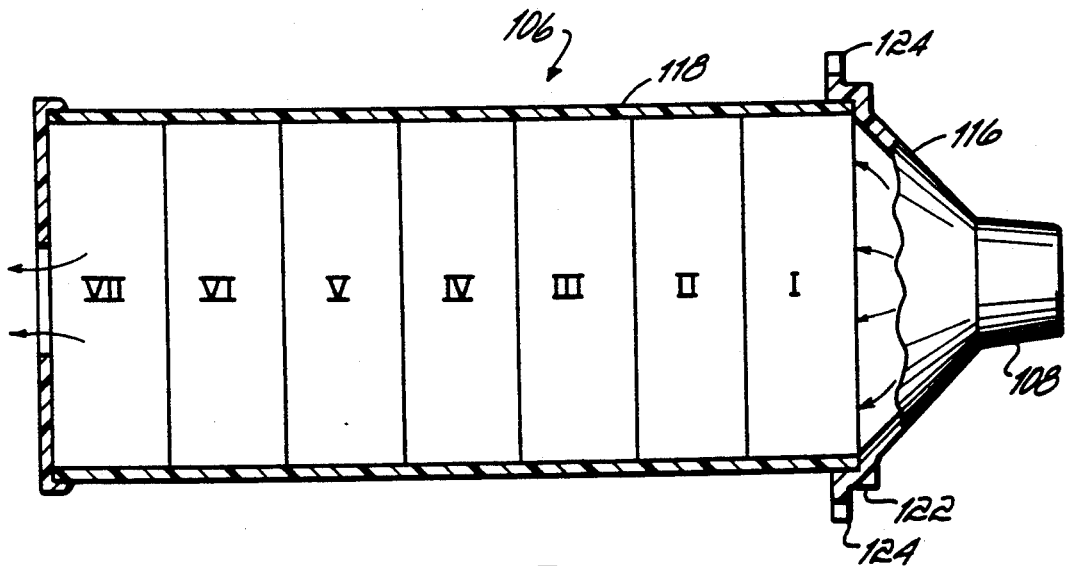
FIG. 5 is a cross-sectional side view of an alternative filter device application.

An alternative filter assembly removes cyanide, formaldehyde and other aldehydes and benzene from an airstream without the use of a separately introduced oxidizing solution. As shown in FIG. 5, filter assembly 106 has an inlet port 108 for receiving a flexible hose, such as the hose 10 shown in FIG. 1. The filter assembly 106 is comprised of a cone portion 116 and a cylindrical portion 118. On cone portion 116 is a raised lip 122 at the point of friction fit connection to the cylindrical portion 118. On this raised lip 122 are a plurality of tabs 124 for mating with slots, such as those shown in FIG. 1 as slots 28.

Inside the cylindrical portion 118 are a variety of spaces for receiving various spacer members, reactive members, and absorptive materials. One material which has been used both as a spacer pad to hold a position in the cylindrical portion, help disperse the airstream, and to serve as the substrate for one or more chemical coatings to render the pad reactive is a 60/40 nylon/polyester composite with a thermoplastic resin as a bonding agent, such as that manufactured by Americo, Inc. The spaces within the filter assembly in FIG. 5, designated I–VII, are filled with layers of desiccant, activated carbon, impregnated or coated pads, and uncoated spacer pads in different configurations. Where desired, one or more spaces can be left empty. The pads are secured in the filter assembly 106 by a bead of hot melt glue around the inside diameter of the cylindrical portion 188. The spaces I–VII are filled with a pad coated or impregnated with a neutralizing or oxidizing agent to remove cyanide, a pad with an aldehyde-removing agent, such as Formalex ™, and a layer of activated carbon to remove benzene and other organic compounds. Typically, a layer of desiccant is placed within the cylindrical portion 118 upstream of the activated carbon layer. Spacer pads with no coating are used to separate and maintain the position of the desiccant and activated carbon layers and to help disperse the airstream, where desired.

In a typical configuration, from the upstream end, (I) is a porous uncoated pad, followed by a porous pad coated with sodium hydroxide solution and dried (II), a porous pad coated with Formalex ™ (III), a layer of desiccant (IV), a spacer pad (V), a layer of activated carbon (VI) and a final spacer pad (VII).

Because the major component of the laser plume is water vapor, there is a risk that moisture levels can rise within the filter assembly 106 to a point where any activated carbon therein loses its activity. Thus, to maximize the absorption time of any activated carbon, it is preferred that a desiccant layer be located upstream of any activated carbon. It has been found that good results can be obtained with the activated carbon at the downstream end of the filter assembly 106, with the desiccant directly upstream. However, it is believed that acceptable results can be obtained even where activated carbon is located near the upstream end of the filter assembly 106. Where the period of moisture buildup is relatively short, the activated carbon layer can be used without the benefit of an upstream desiccant layer. However, as expected, the working lifetime of the activated carbon is shortened.

OPERATING EXAMPLES

The following detailed operating examples illustrate the practice of the invention in its most preferred form, thereby enabling a person of ordinary skill in the art to practice the invention. The principles of this invention, its operating parameters and other obvious modifications thereof will be understood in view of the following detailed procedure.

A filter assembly of the type shown in FIG. 4 was constructed having a cylindrical portion 18 with a ten inch length and four inch inside diameter and made from clear polyvinyl chloride to permit viewing of the filter assembly components. Inside the assembly was an uncoated first dispersal pad 72 and a second dispersal pad 80 coated with Formalex ™. The first dispersal pad was one inch thick and four inches in diameter and made from a nonwoven nylon/polyester blend such as that used for manufacturing industrial floor scrubbing pads. This particular pad material was manufactured by Americo, Inc., Atworth, Ga., and has been used in both wet and dry filter assemblies as a dispersal and spacer pad and as a substrate for an agent reactive to cyanide. The nylon fiber component of this pad has a 60 denier. The polyester fiber components have a range of deniers of 45, 50, 100 and 300. The pad material when used in its scrubbing application is identified as the True Grit ™, green cleaner pad. The second dispersal pad 80 was also obtained from Americo, and the commercial product is identified as the True Grit ™ tan buff pad. The nylon fiber component has a 60 denier. The polyester fiber components have deniers of 25, 45, 50 and 60. This second pad was also one inch thick and four inches in diameter, and coated with Formalex ™, having a total dried weight of 8.0 grams. This pad was typically used as the substrate for the Formalex ™ coating.

An aqueous oxidizing solution of 2.5% sodium lauryl dimethylamine oxide (30% active), 2.5% sodium alpha olefin sulfonate (40% active) and 10% sodium hypochlorite (9.5% active) with the pH adjusted to about 11 by addition of sodium bicarbonate was introduced through feed port 32 at a rate of about 5.5 ml/min over the course of the run. The airstream was conducted into the filter assembly at a flow rate of about 60 SCFM. In a first run, the airstream was injected with *E. Coli* colonies and nutrient to produce a concentration upstream of the filter of about 2.6 billion colonies/min. over a fifteen minute period. In a second run, the airstream was injected with *Serratia Marcescens* and nutrient to produce an upstream concentration of almost one billion colonies/min. over a fifteen minute monitoring period.

After about one minute of operation in both runs, it was observed that the foam generated in the space between the first and second dispersal pads was relatively coarse. Foam was also forming downstream of the second dispersal pad between the inner wall of the cylindrical portion 18 and the outer layer 96 of filter cartridge 86. This foam had a much finer bubble structure, with the consistency of a shaving cream. No foam or visible moisture escaped from the filter assembly during the runs.

Analysis of the airstream exhausted through the filter assembly showed no detectable living bacteria. A series of control runs utilizing the same bacteria in the same concentration without the filter showed substantial amounts of detected living bacteria colonies.

A dry filter assembly as generally shown in FIG. 5 was constructed from a Kraft paper-wrapped tube with a white paper outer layer and an inner coating of paraffin wax. As with the wet filter assembly, the paper tube cylindrical portion 18 had a four inch inside diameter and a ten inch length. The following table shows the removal ability of various configurations of filter components against certain materials typically found in surgery plume. The pads were secured inside the cylindrical portion 18 by a continuous bead of hot melt adhesive on the upstream side.

TABLE 1

| Run | Plume Component Monitored | Filter Configuration | Component Concentration (PPM) Pre-filter | Post Filter |
|---|---|---|---|---|
| | | | (Sampling every 2 min.) | |
| 1 | Hydrogen Cyanide | I Open Cell Urethane Sponge | | |
| | | II Green Pad (uncoated) | 1. 7 | <2 |
| | | III Buff Pad w/Formalex TM | 2. 3.5 | 2 |
| | | IV Anhyd. CaSO4 | 3. 5 | <2 |
| | | V Green Pad (uncoated) | 4. 7 | N.D. |
| | | VI Activated Carbon | | |
| | | VII Green Pad (uncoated) | | |
| | | | (Sampling every 5 min.) | |
| 2 | Formaldehyde | I Green Pad (uncoated) | | |
| | | II Buff Pad w/Formalex TM | 1. 15 | N.D. |
| | | III Green Pad (uncoated) | 2. >25 | 4.5 |
| | | IV Zeolite (Ca Aluminate) | 3. 15 | 1.5 |
| | | V Green Pad (uncoated) | 4. >15 | 4 |
| | | VI Activated Carbon | 5. 20 | 3 |
| | | VII Green Pad (uncoated) | | |
| | | | (Sampling every 2 min.) | |
| 3 | Smoke/ Odor | I Green Pad w/NaOH | Smoke was reduced; Odor not substantially affected | |
| | | II Green Pad (uncoated) | | |
| | | III Zeolite (Ca Aluminate) | | |
| | | IV Green Pad (uncoated) | | |
| | | V Activated Carbon | | |
| | | VI Activated Carbon | | |
| | | VII Green Pad (uncoated) | | |
| | | | (Sampling every 2 min.) | |
| 4 | Hydrogen Cyanide | I Green Pad w/NaOH | 1. >60 | 26 |
| | | II Green Pad w/NaOH | 2. 58 | 30 |
| | | III Buff Pad w/Formalex TM | 3. 47 | 20 |
| | | IV Zeolite (Ca Aluminate) | 4. 45 | 22 |
| | | V Green Pad (uncoated) | | |
| | | VI Activated Carbon | | |
| | | VII Green Pad (uncoated) | | |

The wet filter assembly having the filter cartridge 86 positioned therein has been found to be effective in achieving excellent contact time with the surgery plume component by increasing significantly the surface area through which the surgery plume must pass with minimum drop in the head pressure across the filter assembly. It is estimated that the head pressure drop in this filter assembly is approximately only three percent.

In contrast, testing has been conducted on a hybrid filter assembly having the internal configuration similar to the dry filter, but with injection of an oxidizing solution as in the wet filter. Good results were obtained as to removal of certain particulates, odor-causing species, moisture, and cyanide, formaldehyde, and benzene. However, the reactive agents coated onto the porous pad or sponge tended to become blinded by the volume of fluids inside the filter assembly, which increased the head pressure drop, and in time decreased the filtering efficiency.

Maximum efficiency in removing the odor-causing species from the surgery plume is observed with the wet filter assembly. Though the concentration of suspected carcinogenic/mutagenic agents in a surgery plume can be substantially decreased using the dry filter assembly, residual odor does carry through.

Thus is it apparent that there has been provided, in accordance with the invention, a filter assembly and method of filtering which fully satisfies the objects, aims, and advantages set forth above. While the invention has been described in conjunction with specific embodiments thereof, it is evident that many alternatives, modifications, and variations will be apparent to those skilled in the art in light of the foregoing description. Accordingly, departures may be made from such details without departing from the spirit or scope of the general inventive concept.

I claim:

1. A filter assembly for receiving and treating an airstream containing a gaseous and particulate materials from a surgery plume, comprising:
   a canister having an inlet and an outlet, said inlet adapted to receive an airstream containing gaseous and particulate materials from a surgery plume;
   introducing means for introducing an aqueous solution comprises of oxidizing and surface active components downstream of said canister inlet;
   a first porous member means in said canister for receiving said aqueous solution and said gaseous and particulate materials and for generating a foam by interaction of said aqueous solution and said airstream through said porous member, the first porous member means being located downstream of said introducing means; and
   activated carbon in said canister downstream of said inlet through which said airstream flows.

2. The filter assembly of claim 1 further comprising a second porous member downstream of said first porous member and spaced therefrom to create between said first and second porous members a foam receiving chamber.

3. The filter assembly of claim 1 further comprising moisture removing material in said canister upstream of said outlet.

4. The filter assembly of claim 3 wherein said moisture removing materials is selected from the group consisting of calcium sulfate, amorphous silica, zeolite, and mixtures thereof.

5. The filter assembly of claim 1 further comprising a discrete porous member containing a component thereon for removing aldehyde from said airstream.

6. The filter assembly of claim having means to draw gaseous and particulate materials generated during electrocautery into said canister.

7. The filter assembly of claim 1 wherein said activated carbon is downstream of said first porous member.

8. The filter assembly of claim 1 wherein said activated carbon is granulated charcoal.

9. The filter assembly of claim 1 wherein said activated carbon is comprised of a mixture of ground activated carbon and adhesive impregnated onto a non-woven substrate.

10. The filter assembly of claim 9 wherein said activated carbon comprises a portion of a discrete filter cartridge, said filter cartridge located inside said canister.

11. The filter assembly of claim 10 wherein said filter cartridge has a tubular construction and further comprises a layer of a non-woven substrate impregnated with a mixture of amorphous silica and adhesive.

12. The filter assembly of claim 11 wherein said filter cartridge includes an open space along the entire center length thereof to facilitate passing said airstream out of said filter assembly.

13. The filter assembly of claim 1 wherein said first porous member is comprised of a blend of nylon and polyester fibers.

14. A filter assembly for receiving and treating an airstream containing gaseous and particulate materials including cyanide, aldehyde and benzene from a surgery plume, comprising:
   a canister having an inlet and an outlet, said inlet adapted to receive an airstream containing gaseous and particulate materials from a surgery plume;
   a filter member inside said canister incorporating a component reactive to cyanide downstream of said inlet;
   a discrete desiccant layer inside said canister downstream of said filter component reactive to cyanide;
   a filter member inside said canister incorporating a component reactive to aldehydes downstream of said inlet; and
   a discrete layer of activated carbon downstream of said desiccant layer for removing said benzene.

15. A system for receiving and treating an airstream containing gaseous and particulate materials from a surgery plume, comprising:
   a canister having a flow path defined between an inlet and an outlet of the canister wherein an airstream is received through the inlet, treated within the canister and exhausted from the outlet, said inlet for receiving said airstream containing gaseous and particulate materials from said surgery plume;
   said canister having a means for introducing an aqueous solution comprised of oxidizing and surface active components for treating the airstream;
   a first filter component in said canister downstream of said inlet which is positioned to receive said aqueous solution and said airstream containing said gaseous and particulate materials, the first filter component having porous means for generating a foam through interaction of said aqueous solution and said airstream in said porous means; and
   an activated carbon filter component in said canister positioned downstream of said inlet in a flow path through which the airstream flows.

16. The system of claim 15 wherein said oxidizing component of said aqueous solution is selected from the group consisting of sodium hypochlorite, sodium perborate, sodium permanganate, sodium thiosulfate, and mixtures thereof.

17. The system of claim 15 wherein said surface active component of said aqueous solution is selected from the group consisting of sodium alpha olefin sulfonate, sodium lauryl dimethylamine oxide, sodium alpha olefin sulfate, nonylphenol polyethylene glycol ether, disodium oxy-bis dodecyl benzene sulfonate, and mixtures thereof.

18. The system of claim 15 wherein the pH of said aqueous solution is in the range of about 10.5 to about 12.5.

* * * * *

UNITED STATES PATENT AND TRADEMARK OFFICE
CERTIFICATE OF CORRECTION

PATENT NO. : 5,288,469
DATED : February 22, 1994
INVENTOR(S) : Randy Marc Skalla It is certified that error appears in the above-indentified patent and that said Letters Patent is hereby corrected as shown below:

Column 5, line 27, the sentence beginning with "The oxidizing component" should begin a new paragraph.
Column 5, line 38, "lycol" should be --glycol--.
Column 6, line 9, "desiccant" should be --desiccant layer--.
Claim 1, Column 13, line 2, "a gaseous" should be --gaseous--.
Claim 6, Column 13, line 35, "of claim having" should be --of claim 1 having--.
Claim 15, Column 14, line 29, "from said surgery" should be --from a surgery--.

Signed and Sealed this

Twenty-fourth Day of January, 1995

BRUCE LEHMAN

*Attest:*

*Attesting Officer*  *Commissioner of Patents and Trademarks*